United States Patent
Rolfes Meyering et al.

(10) Patent No.: US 9,649,405 B2
(45) Date of Patent: May 16, 2017

(54) FIBROIN-CONTAINING HYDROGELS FOR PELVIC TISSUE TREATMENT

(71) Applicant: Boston Scientific Scimed, Inc., Maple Grove, MN (US)

(72) Inventors: Emily R. Rolfes Meyering, Saint Louis Park, MN (US); Benjamin Y. Arcand, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/653,984

(22) PCT Filed: Dec. 20, 2013

(86) PCT No.: PCT/US2013/077090
§ 371 (c)(1),
(2) Date: Jun. 19, 2015

(87) PCT Pub. No.: WO2014/100666
PCT Pub. Date: Jun. 26, 2014

(65) Prior Publication Data
US 2015/0314035 A1 Nov. 5, 2015

Related U.S. Application Data

(60) Provisional application No. 61/745,361, filed on Dec. 21, 2012.

(51) Int. Cl.
*A61F 2/02* (2006.01)
*A61L 24/04* (2006.01)
(Continued)

(52) U.S. Cl.
CPC .......... *A61L 24/043* (2013.01); *A61F 2/0022* (2013.01); *A61F 2/0045* (2013.01);
(Continued)

(58) Field of Classification Search
CPC ...................................................... A61F 2/02
See application file for complete search history.

(56) References Cited

U.S. PATENT DOCUMENTS

2004/0259023 A1* 12/2004 Campagnola ........ A61K 6/0052
430/270.1
2006/0058578 A1* 3/2006 Browning .......... A61B 17/0401
600/37

(Continued)

FOREIGN PATENT DOCUMENTS

WO WO 2007/097994 A2 8/2007
WO WO 2011/031854 A1 3/2011
WO WO 2012/135699 A1 10/2012

OTHER PUBLICATIONS

Extended European Search Report for corresponding European Application No. 13866282.0, dated Sep. 28, 2016 (9 pages).

*Primary Examiner* — Christine H Matthews
(74) *Attorney, Agent, or Firm* — Bookoff McAndrews, PLLC (57) ABSTRACT

Compositions, systems, and methods for the treatment of pelvic tissue conditions that include use of a silk fibroin-containing hydrogel composition are disclosed. The composition may include a water-soluble fibroin and a water-soluble crosslinkable polymer that can be used as a pre-formed hydrogel, and/or delivered to a pelvic tissue site and crosslinked in situ to form a hydrogel. The composition may promote tissue closure, such as vaginal wound or fistula closure; and/or enhance attachment or anchoring of a pelvic implant to a pelvic tissue. The composition may be a hydrogel that is delivered to a pelvic tissue site, formed at the site in situ, and/or associated with a portion of the implant (e.g., a mesh implant) via a tether or implant extension portion, thereby providing improved immobilization of the implant. Systems or kits that include the com- (Continued)

position and/or a delivery needle or insertion tool are also described.

20 Claims, 4 Drawing Sheets

(51) Int. Cl.
    *A61F 2/00*     (2006.01)
    *A61N 5/06*     (2006.01)
    *A61L 24/00*     (2006.01)
    *A61K 9/00*     (2006.01)
    *A61L 31/04*     (2006.01)
    *A61L 31/10*     (2006.01)
    *A61L 31/14*     (2006.01)
    *A61L 31/16*     (2006.01)

(52) U.S. Cl.
    CPC .......... *A61K 9/0024* (2013.01); *A61L 24/001* (2013.01); *A61L 24/0015* (2013.01); *A61L 24/0031* (2013.01); *A61L 31/041* (2013.01); *A61L 31/10* (2013.01); *A61L 31/145* (2013.01); *A61L 31/16* (2013.01); *A61N 5/062* (2013.01); *A61F 2210/0061* (2013.01); *A61F 2210/0085* (2013.01); *A61L 2300/412* (2013.01); *A61L 2300/802* (2013.01)

(56) References Cited

U.S. PATENT DOCUMENTS

| | | |
|---|---|---|
| 2008/0312315 A1 | 12/2008 | Daniloff et al. |
| 2009/0182190 A1 | 7/2009 | Dann |
| 2011/0052695 A1 | 3/2011 | Jiang et al. |
| 2011/0144373 A1* | 6/2011 | Swan .................... C07C 309/42 560/25 |

* cited by examiner

Fig. 1A

Trimethylolpropane Ethoxylate Triacrylate

Fig. 1B

Tetramethylolpropane Ethoxylate Tetraacrylate
4-Arm PEG Tetraacrylate

Fig. 1C

PEG Diacrylate

Fig. 1D

PEG Dimethacrylate

Fig. 1E

Tetraethylene glycol diacrylate

FIBROIN-CONTAINING HYDROGELS FOR PELVIC TISSUE TREATMENT

PRIORITY CLAIM

This application claims the benefit from International Application No. PCT/US2013/077090, filed Dec. 20, 2013, which in turns claims the benefit under 35 U.S.C. §119(e) from United States Provisional Patent Application having U.S. Ser. No. 61/745,361, filed Dec. 21, 2012, entitled "FIBROIN-CONTAINING HYDROGELS, COMPOSITIONS, ARTICLES, AND METHODS FOR PELVIC TISSUE TREATMENT", the disclosures of which are incorporated herein by reference in their entireties.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Various treatments have been used to address these and other pelvic ailments. For example, implantable surgical meshes have been used for hernia repair and pelvic floor tissue repair. Urethral slings have been used for treating fecal and urinary incontinence. and many others. Other treatments involve the use of bulking agents and tissue adhesives.

There is a desire for improved compositions and systems for the treatments of pelvic floor disorders. Challenges in this area of technology include maintaining proper positioning of an implant following placement and improving tissue healing in the implant area. The invention provides improved compositions and systems for the treatment of pelvic floor disorders using silk fibroin-containing hydrogel compositions.

SUMMARY

Generally, the invention relates to compositions, systems, and methods for the treatment of pelvic tissue disorders that include use of a silk fibroin-containing hydrogel composition.

In some embodiments the invention provides a pelvic tissue treatment composition comprising water-soluble fibroin and a water-soluble crosslinkable polymer. The composition can be used in various systems and methods for treatment of a pelvic tissue disorder.

For example, in some embodiments the invention provides a method for treating a pelvic tissue comprising steps of applying the hydrogel composition to a pelvic tissue; and then treating the composition to cause crosslinking of the water-soluble crosslinkable polymer and formation of a fibroin-containing hydrogel in association with the tissue. Exemplary compositions include a photo polymerization initiator, and the treatment step includes irradiating the composition at the site the composition is applied to. The hydrogel formed at the tissue site can provide a tissue sealant function and/or can enhance the growth of tissue at the treatment site to provide improve healing and a better therapeutic outcome.

Some embodiments of the invention provide a method to enhance the closure and healing of a pelvic tissue, the method comprising steps of applying the composition to a tissue that has been surgically manipulated; and treating the composition to cause crosslinking of the water-soluble crosslinkable polymer and formation of a fibroin-containing hydrogel which acts as a tissue sealant to close and heal the surgically-manipulated tissue.

The composition can optionally include bioactive agents, such as proteins or peptides, to enhance the tissue response.

In other embodiments the hydrogel composition is cross-linked prior to delivering to a target pelvic tissue site. The hydrogel composition can be in a dried, partially hydrated, or fully hydrated form when delivered to the tissue site. If the hydrogel is at least partially dehydrated, body fluid can cause swelling of the hydrogel at the tissue site, and in some cases the swelling can be useful in providing a therapeutic effect.

In some embodiments, the invention provides a system and method for enhancing the attachment of a mesh to the tissue. The system comprises water-soluble fibroin, a water-soluble crosslinkable polymer, and a mesh implant. The method comprises steps of placing all or a portion of a mesh at a tissue site; applying the composition to all or a portion of the tissue wherein the composition contacts the mesh and the tissue; and treating the composition to cause crosslinking of the water-soluble crosslinkable polymer and formation of a fibroin-containing hydrogel which acts as an adhesive to enhance the attachment of a mesh to the tissue. Steps of applying and/or treating can be performed before or after the mesh is placed at the tissue site.

In other embodiments, the invention provides a system and method for a pelvic tissue anchoring. The system comprises water-soluble fibroin, a water-soluble crosslinkable polymer, and a tether attached or attachable to the hydrogel matrix formed from the fibroin and polymer components. In some embodiments, a composition including the fibroin and polymer components can be delivered to, and then crosslinked at tissue site to form the anchor. In other embodiments, the composition can be in crosslinked form prior to delivering to a target pelvic tissue site. The system can also include a needle and/or composition delivery conduit to provide the composition or crosslinked hydrogel at a desired tissue site. After the crosslinked hydrogel is delivered to or formed at the target site it serves as a tissue anchor to assist in immobilization and/or placement of an article (e.g., a mesh implant).

In some embodiments the composition is used to for the treatment of surgically manipulated vaginal tissue, and the composition is used to promote vaginal wound closure. In some embodiments the composition is applied to surgically manipulated pelvic tissue involving an entervaginal fistula, or a fecal or anal fistula, and the composition is used to promote tissue closure of the treated fistula.

The composition of the invention, used alone or in combination with one or more other system components, provides one or more advantages for pelvic tissue treatment. For example, the composition can be supple (not brittle) and easy to apply to a tissue site; the composition can provide better control over hydrogel formation as compared to spontaneously polymerizable material; the composition can provide better biocompatibility; the composition can provide improved treatment for elastic or mobile tissues; in some embodiments the composition can provide better immobilization of the and implant, and can also provide better healing of surgical site.

DETAILED DESCRIPTION

The hydrogel-forming composition includes a silk protein (i.e., silk fibroin). Natural silk is a filamentous product secreted by an organism, with fibroin being the primary structural component of silk. Fibroin is composed of monomeric units comprising heavy and light chains, and a protein derived from the P25 gene.

Fibroin can be obtained from natural materials producted by an organism (e.g., a silkworm), such as raw cocoons. The material can be degummed to remove sericin prior to making a fibroin solution. Various materials and methods can be used for removal of sericin; extractants include urea solution, hot water, enzyme solutions such as papain can remove sericin from fibroin. Mechanical methods such as ultrasound, abrasive scrubbing and fluid flow can also be used to remove sericin. Methods for performing sericin extraction have been described in U.S. Publication No. 2003/0100108.

Silk fibroin can be prepared by treatment of naturally-occurring fibrous silk with a dissolution agent, such as, e.g., a chaotropic agent. For example, as described in U.S. Pub No. 20110052695, dissolved silk can be generated in the presence of lithium bromide at an elevated temperature (e.g., a 4 hour digestion at 60° C. in a 9.3 M aqueous solution of lithium bromide; pure silk fibroin at a concentration of 200 g/L to a silk concentration of 20% (w/v)). The treatment can provide uniformly and repeatably dissociated silk fibroin molecules to ensure similar fibroin solution properties.

The composition can also include fibroin fragments or degradation products of fibroin. For example, silk fibroin can be enzymatically treated with proteolytic enzymes such as chymotrypsin, actinase, and carboxylase (e.g., see, Chen, K., et al. (1991) J. Seric. Sci. Jpn. 60, 402-403 and Chen, K., et al. (1996) J. Seric. Sci. Jpn. 65, 131-133) to generate lower molecular weight product of fibroin. The lower molecular weight fibroin products can be included in the hydrogel-forming composition. In some embodiments, the composition includes a mixture of lower molecular weight fibroin products (such as prepared by enzymatic digestion) and non-digested fibroin. For example, the lower molecular weight components could be a minority (less than 50% wt) of the weight of the fibroin component in the composition, such as in the range of about 1% wt to about 40% wt, about 1% wt to about 30% wt, about 1% wt to about 20% wt, about 1% wt to about 10% wt, or about 1% wt to about 5% wt, of the weight of the total fibroin component in the composition, with the remaining amount of fibroin being in undigested form.

Use of a composition including undigested and digested fibroin can provide a combination of desirable properties in the hydrogel. The undigested fibroin can improve hydrogel properties relating to tensile strength and elastic modulus. The digested fibroin can promote cellular responses associated with new tissue formation, such as the production of extracellular matrix components (e.g., collagen and fibronectin) and cytokines (e.g., transforming growth factor-beta1). The lower molecular weight digested fibroin products may also be released from the hydrogel to provide a more rapid local tissue response that promotes healing.

In exemplary embodiments, the silk fibroin component of the composition (wherein the silk fibroin is in undigested form, in digested form, or in a mixture of undigested and digested forms) is present in the hydrogel-forming composition in the range of about 5% (w/v) to about 75% (w/v) to about, about 10% (w/v) to about 50% (w/v), or more specifically about 15% (w/v) to about 40% (w/v).

The hydrogel-forming composition includes a hydrogel forming material. The hydrogel forming material can be a crosslinkable compound, such as a crosslinkable small molecule, oligomer or polymer. The crosslinkable compound can contains two or more crosslinkable groups. Exemplary crosslinkable groups include free radical groups such as acrylates and methacrylates.

Exemplary hydrogel-forming materials containing polymerizable groups include small molecules and polymers. Examples of polymerizable small molecules include reagents such as trimethylolpropane triacrylate, trimethylolpropane trimethacrylate, trimethylol propane tetraacrylate, monosaccharide acrylates, oligosaccharide acrylates, tetraethylene glycol diacrylate, and zinc acrylate. Exemplary polymerizable small molecules can be in solid or liquid form.

Other exemplary hydrogel-forming materials containing polymerizable groups are polymerizable polymers such as trimethylolpropane ethoxylate triacrylate, multi-arm polyethylene glycol (PEG) acrylates, multi-arm PEG dimethacrylates, PEG diacrylates, PEG dimethacrylates, polypropylene glycol (PPG) diacrylates, PPG dimethacrylates, starch acrylates and methacrylates, polysaccharide acrylates and methacrylates, and the like. Polymerizable polymers can also be formed using other hydrophilic polymers such as poly(vinylpyrrolidone) (PVP), poly(ethylene oxide) (PEO), poly(ethyloxazoline), poly(propylene oxide) (PPO), poly(meth)acrylamide (PAA) and poly(meth)acrylic acid, poly(ethylene glycol) (PEG), PEG-PPO (copolymers of polyethylene glycol and polypropylene oxide), hydrophilic segmented urethanes, and polyvinyl alcohol. These polymerizable polymers can be in solid or liquid form. Partial structures for some exemplary polymerizable materials are shown in FIGS. 1A-1E.

Other exemplary hydrogel-forming materials are those prepared from a hydroxy-functional compound. Typically, the hydroxy-functional compound has at least 2 hydroxyl groups, and more specifically about 2 to 4 hydroxyl groups per molecule. The hydroxyl groups are derivatized to provide free-radical-reactive groups, or polymerizable groups, and therefore can provide a defined, limited number of reactive groups. In some embodiments a hydroxy-functional compound is derivatized to provide a second component that has two amine-reactive groups.

Depending on the chemical material used, these resulting matrices may be biostable, or biodegradable following a period of implantation.

The hydrogel-forming composition can also include a polymerizable polypeptide. A polypeptide refers to an oligomer or polymer including two or more amino acid residues, and is intended to encompass compounds referred to in the art as proteins, polypeptides, oligopeptides, peptides, and the like.

In some cases, the polymerizable polypeptide can be based on a matrix protein, or a portion thereof. The matrix protein, or portion thereof, can be a cell attachment factor. Exemplary cell attachment factors include those selected from fibronectin, vitronectin, laminin A, laminin B1, laminin B2, collagen I, and thrombospondin. Exemplary active portions of cell attachment factors include polypeptides selected from RGDS, LDV, REDV, RGDV, LRGDN, IKVAV, YIGSR, PDSGR, RNIAEIIKDA, RGDT, DGEA, GTPGPQGIAGQRGVV, RGD, VTXG, and FYVVMWK.

In exemplary embodiments, (non-silk fibroin) hydrogel-forming material is present in the hydrogel-forming composition in the range of about 25% (w/v) to about 95% (w/v) to about, about 50% (w/v) to about 90% (w/v), or more specifically about 60% (w/v) to about 85% (w/v).

The hydrogel-forming composition can also include one or more components to promote the crosslinking of the crosslinkable compound. For example, the composition can include at least one chemical initiator, such as a photoinitiator. The photoinitiator can be treated with radiation to initiate the crosslinking reaction.

Photoinitiators are compounds that convert absorbed light energy, UV or visible light, into chemical energy in the form of initiating species, via free radicals or cations. Based on the mechanism in which initiating radicals are formed, photoinitiators are generally divided into two classes: Type I and II photoinitiators. Type I photoinitiators undergo a unimolecular bond cleavage upon irradiation to yield free radicals. Type II photoinitiators undergo a bimolecular reaction where the excited state of the photoinitiator interacts with a second molecule (a coinitiator) to generate free radicals.

Examples of initiators include 4-hydroxybenzophenone, 2-hydroxy-4'-(2-hydroxyethoxy)-2-methylpropiophenone, 2,2-dimethoxy-2-phenylacetophenone, 4-aminobenzophenone, acetophenone, 2,2-diethoxyacetophenone and more. Photoinitiators that may be used include those from the family of benzophenones, anthraquinones, benzoins, acetophenones and some of the phosphate and antimonate salts.

In other preparations, the composition can include an oxidizer and reductant if crosslinking of the crosslinkable compound is initiated by a REDOX reaction. Exemplary oxidizer and reductant include peroxides and transition metal sugar conjugates, such as hydrogen peroxide and ferrous lactate.

The compositions that include the matrix forming material can include one or more other non-matrix forming materials, such as buffers, excipients, and/or bioactive agents. The pH of the compositions can be controlled by buffering using conventional buffering materials such as phosphate, borate, and bicarbonate buffers. In embodiments, the pH is controlled between about 7 to about 8, which is beneficial for use with many sensitive bioactive agents, although other pH values may be suitable for certain applications.

Other polymers or non-polymeric compounds can be included in the mixture that can change or improve the properties of the matrix. These optional compounds can change the elasticity, flexibility, wettability, or adherent properties, (or combinations thereof) of the formed matrices.

Exemplary optional components include a plasticizing agent a mixture of plasticizing agents. Suitable plasticizing agents include glycerol, diethylene glycol, sorbitol, sorbitol esters, maltitol, sucrose, fructose, invert sugars, corn syrup, and mixtures thereof. The amount and type of plasticizing agents can be readily determined using known standards and techniques.

Optionally, the hydrogel can be associated with a pharmaceutical agent designed to provide a therapeutic effect to tissue at the site the hydrogel is localized or formed. For example, the pharmaceutical agent can be released from the hydrogel by diffusion, or released by the degradation of the hydrogel matrix, for treatment of a target tissue. In some aspects the chemical material can include a bioactive agent that is a macromolecule, such as polypeptide, polysaccharide, or polynucleotides. The material can also include bioparticles, such as viral particles, and cells, such as prokaryotic cells or eukaryotic cells. In some embodiments, the materials of the invention can optionally be used in a gene therapy method in a subject. The optional method can involve the release of a polynucleotide from the matrix, and the effect of the polynucleotide on a tissue or cell to produce a biological effect. For example, the polynucleotide can be used to treat a disease by reducing the expression of a gene encoding a target protein.

Exemplary classes of active agents include: growth factors, pro-angiogenesis factors, anti-fibrotic agents, anti-microbial agents, antibiotics, immuno-suppressive agents, inhibitors of epithelial cell activation and/or migration, compounds that enhance wound regeneration, estrogen, other hormones, immunosupressants, anti-inflammatory agents, anti-cancer drugs, etc. For example, the active agent can comprise the ovarian steroid, estrogen or Estradiol for pelvic tissue treatment.

An exemplary drug-releasing implant is described in commonly assigned WO 2012/116182, which describes an multilayered film implant comprising three or more therapeutic agent-containing layers and two or more intermediate regulating layers that are different than the therapeutic agent-containing layers and that modulate release of the therapeutic agent from the film, each intermediate layer positioned between two therapeutic agent-containing layers.

In some embodiments the components of the hydrogel-forming composition are provided to a user in the form of a system or kit. The components (e.g., crosslinkable compound, crosslinking initiator, solvent, etc.) can be provided separately in the system, or, in some cases, can be combined (e.g., the crosslinkable compound is dissolved in a solvent, optionally with a crosslinking initiator).

In other embodiments, the crosslinkable chemical system is applied to the device, or the device is implanted and the surgeon applies the chemical system to the device and tissue for adherence.

In other embodiments, components of the hydrogel composition are pre-crosslinked to form a hydrogel that can be provided to a user in a system or kit. For example, the crosslinked hydrogel can exist as a hydrated structure in moisture in a package or as a dried (e.g., lyophilized or dessicated) form for shipping and/or storage. If rehydration is required for use, such as tissue attachment, a rehydration step can be performed in a suitable solution (e.g., saline bath) or rehydration of the lyophilized or dessicated gel can occur following placement in the body at a desired anatomical tissue site.

The hydrogel can be provide in a particular shape in the system, such as in the form of filaments, strings, tubes, cotton-like puffs, helices or bubbles. If rehydration is required for optimal tissue attachment, it can be performed prior to placement (such as in an operating room) using a saline injection, or rehydration can occur by the anatomical tissues themselves.

In some cases the hydrogel or hydrogel-forming composition can be in a dried or solid form but encapsulated by a quickly dissolving polymer, such as methylcellulose or tappioca-like starch. For example, encapsulated hydrogel or hydrogel-forming composition can be part of an anchoring system.

In use, the encapsulated hydrogel is delivered to the target pelvic tissue, where, during delivery, the encapsulating polymer protects the hydrogel from hydration. At the target site the encapsulating polymer completely dissolves and the hydrogel absorbs body fluid at expands at the target site, resulting in improved immobilization of the hydrogel.

The fibroin-containing hydrogel composition can be used in conjunction with medical implants, such as mesh, to enhance fixation to tissues thereby providing tissue support utilizing planar reinforcement elements. For example, the hydrogel composition can (1) improve fixation of the implant in place to provide tension and/or support to anatomical structures, and/or (2) maintain the implant location relative to tissues to prevent migration, bunching and erosion and to facilitate tissue in-growth.

In other embodiments the fibroin-containing hydrogel composition is crosslinkable and applied as a coating on a medical device to act as an adhesive to bond to the tissue for fixation purposes. The crosslinked hydrogel can provide a temporary structure and matrix to support forces needed for surgical repair. For example, as tissue healing occurs, cellular in-growth into the chemical matrix provides a scaffold to promote surgical wound healing. In some cases, the hydro gel composition can provide a tacky surface on the surgical implant that allows for easier device placement, which can minimize or eliminate the device springing back or sliding off the tissue structures that are being fixated.

The fibroin-containing hydrogel composition can be used with any pelvic implant. In some constructions, the hydrogel composition is used with an implant for treating incontinence, prolapse, or a mixture of incontinence and prolapse. The implant can includes a portion useful to support the urethra or bladder neck to address urinary incontinence, such as described in commonly assigned application published as US 2010/0256442 (Ogdahl, et al.), and exemplified by the mesh constructions of FIGS. 3B and 3C therein. In some constructions, the hydrogel composition is used with a mesh that is configured to treat pelvic conditions by supporting levator muscle, such as described in commonly assigned application published as US 2010/0261952 (Montpetit, et al.). Commonly assigned application published as US 2011/0034759 (Ogdahl, et al.), also describes implants that include extension portions, and transvaginal methods for inserting the mesh into a patient. In some constructions, the hydrogel composition is used with a mesh configured to treat vaginal prolapse, including anterior prolapse, posterior prolapse, or vault prolapse such as described in commonly assigned application published as US 2010/0261955-A1 (O'Hern, et al.).

The hydrogel composition can be used on a nonabsorbable (biostable) mesh material made from a single or a combination of biostable materials. Exemplary nonabsorbable materials include synthetic polymers such as polyamides (e.g., nylons), fluoropolymers (e.g., polytetrafluoroethylene (PTFE) and polyvinylidene fluoride (PVF)), and polyolefins (e.g. polypropylene and polyethylene). In some aspects, polypropylene is used as a nonabsorbable material to form the mesh. Exemplary constructions use polypropylene, including isotactic and syndiotactic polypropylene, or blends thereof, to form the mesh. In some embodiments the implant has a knitted or woven construction using polypropylene monofilaments (see, for example, U.S. Pat. No. 4,911,165). The mesh can be constructed from a monofilament or a multifilament yarn. Optionally, a non-knitted/non-woven (e.g., molded) polypropylene mesh layer (see, for example, commonly assigned PCT Publication Nos. WO2011/063412 and WO2011/072148) can be used.

The hydrogel composition can also be used on a biodegradable mesh material made from a single biodegradable materials or a combination of biodegradable materials. For example, the composition can be applied to a knitted or woven construction using monofilaments formed of a biodegradable material, or combination of biodegradable materials. Alternatively, the mesh can be formed from a molding process.

Biodegradable materials include biodegradable homopolymers, biodegradable copolymers, and blends of biodegradable polymers. Degradation of the mesh can occur by using a mesh made from a polymer that has hydrolytically unstable linkages in the backbone. These most common hydrolytically unstable chemical groups in vivo are esters, anhydrides, orthoesters, and amides.

For construction of a biodegradable mesh, biodegradable homopolymers and copolymers can be formed from monomers such as glycolide, lactide, and stereoisomers thereof, ϵ-caprolactone, valerolactone, hydroxybutyric acid, hydroxypentanoic acid, trimethylene carbonate, and dioxanone. Exemplary biodegradable polymers include polyhydroxyalkanoates (e.g., poly-4-hydroxybutyrate (P4HB), poly(3-hydroxyvalerate), poly(hydroxybutyrate-co-hydroxyvalerate); polyesters (e.g., poly(L-lactide) (LPLA), poly(DL-lactide) (DLPLA); poly(L-lactide-co-glycolide) (LPLG); poly(DL-lactide-co-L-lactide) (LDLPLA); poly(glycolide-co-trimethylene carbonate) (PGA-TMC); poly(DL-lactide-co-glycolide) (DLPLG); poly(ϵ-caprolactone) (PCL); poly(valerolactone); poly(glycolic acid); poly(glycolide) (PGA); and poly(dioxanone) (PDO); polyorthoesters; polyalkeneanhydrides, e.g., poly(sebacic acid); polyanhydrides, and polyphosphazine.

The hydrogel composition can also be used on a mesh made from a combination of non-absorbable and absorbable polymeric materials, such as in commonly assigned WO 2012/048105, which describes a transvaginal mesh implant with a first non-absorbable mesh layer and a second absorbable layer, or in commonly assigned WO 2011/103141, which describes an mesh including absorbable fibers and non-absorbable fibers, as well as a porous mesh of non-absorbable fibers interwoven or knit to produce a porous mesh with absorbable polymer filled at openings in the mesh, or intersection of the fibers.

The hydrogel composition can be applied to the mesh prior to, or after the mesh is placed at a tissue site in the pelvic area. For example, in some embodiments the hydrogel composition is applied all or a portion of the mesh prior to placement of the mesh at a tissue site. In some cases, the composition is applied to a portion(s) of the mesh where a stronger attachment to the tissue is desired. On the mesh the hydrogel composition can be uncrosslinked, partially crosslinked, or fully crosslinked prior to placing the mesh at a tissue site. If the hydrogel is uncrosslinked or partially crosslinked it can be treated after placement (e.g., by UV irradiation or application of an initiator composition) to initiate or further crosslink the composition.

If the hydrogel composition is applied to the mesh after mesh placement, the composition can be delivered to one or more desired portions of the mesh and then treated to crosslink the composition and adhere the mesh to the tissue. Any one or more of a variety of methods can be used to deliver the composition to a target area on the mesh depending on how and where the mesh is placed on the tissue. For example, the composition can be brushed (e.g., painted) or sprayed on the placed mesh if the tissue if the application site is readily accessible. In other cases, a delivery conduit (a hollow needle or cannula) can be used to inject the composition to an internal site where the mesh is located. Crosslinking at an internal site can be initiated by using a light source that is able to reach the internal site (e.g., a needle with an optic fiber or distal end with a UV light source), or an initiator composition that is injected at the internal site.

In some modes of practice the fibroin-containing hydrogel composition is used as an alternative to, or in combination with, a suture or a tissue fixation anchor. The use of the hydrogel composition as a tissue anchor can improve implant stabilization, among other benefits. In some cases, the fibroin-containing hydrogel composition can be a part of a tissue anchor that is introduced at a target tissue location and expands by hydration within the tissue to secure the anchor at the target location.

Anchored in a tissue, the hydrogel composition can be used to assist in the immobilization of an implant that is associated with the composition. A portion of the implants, such as a mesh portion or a connector material, can be present between the hydrogel anchor and a support portion of the implant. For example, in some cases an extension portion of a mesh implant extends from a central support portion and to the hydrogel anchor, with the distal portion of the extension attached (e.g., by adherence) to the hydrogel anchor. The hydrogel anchor with attached distal extension portion can be formed prior to placement in the body (for example, the end can be placed in a liquid hydrogel composition which can then be crosslinked), or the attachment can be performed in the body, by polymerizing the composition in situ which the distal end of the extension is within the composition.

Other extension or connector portions of the implant can have a non-mesh structure. Non-mesh extension or connector portions can, in some cases, be made from one or more hydrogel anchor materials, such as silk fibroin, or hydrophilic polymer.

Figure 1A:
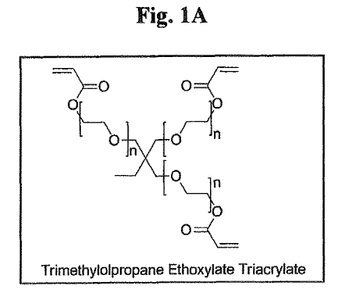
FIGS. 1a-e illustrate exemplary chemical structures of hydrogel-forming material that can be used in compositions of the invention.
Figure 1B:
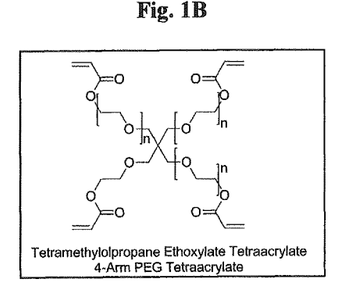
Figure 1C:
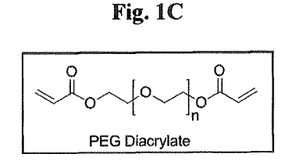
Figure 1D:
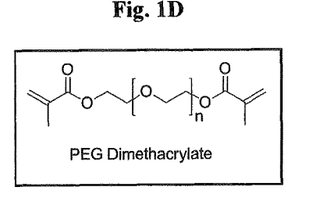
Figure 1E:
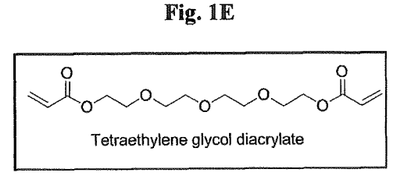
Figure 2A:
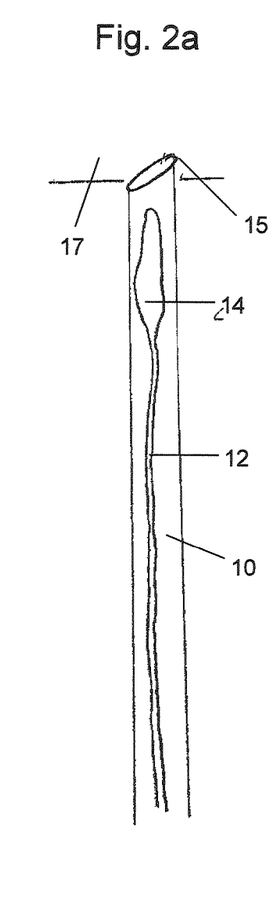
FIGS. 2a-c illustrate parts of a hydrogel anchoring system and steps of forming the hydrogel anchor within tissue.
Figure 2B:
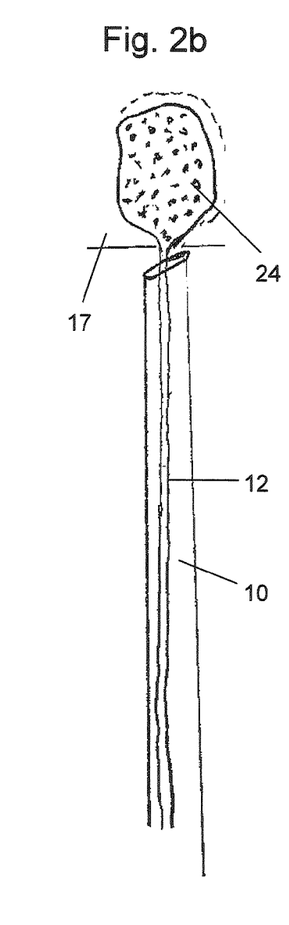
Figure 2C:
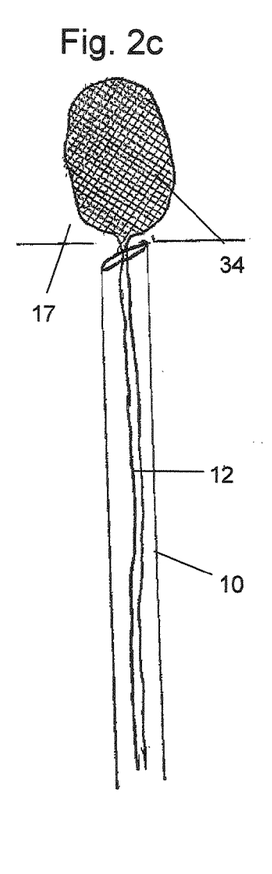

FIGS. 2a-c illustrate embodiments of a silk hydrogel tissue anchor, and insertion of the hydrogel anchor into a target tissue. FIG. 1a shows a tissue needle 10 having a lumen in which a tissue anchor having a silk hydrogel distal end 14 and an implant tether 12, which are sized to fit in the lumen. The tether 12 can be made of a material that connects the hydrogel distal end to another portion of the implant. For example, the tether can connect the hydrogel and a mesh portion that supports tissue. In some cases the tether can be made of a mesh material and can support tissue. Within the lumen the silk hydrogel can be in a dehydrated form to minimize its size.

Sharpened distal end 15 of the tissue needle 10 is shown penetrating a pelvic tissue 17. FIG. 2b shows that upon entry into the tissue the silk hydrogel expands to form a swollen hydrogel 24 that expands and places pressure on the surrounding tissue to exert its anchoring effect. FIG. 2c shows that the expanded hydrogel 34 can provide a mesh like anchoring property at the tissue site.

Figure 3A:
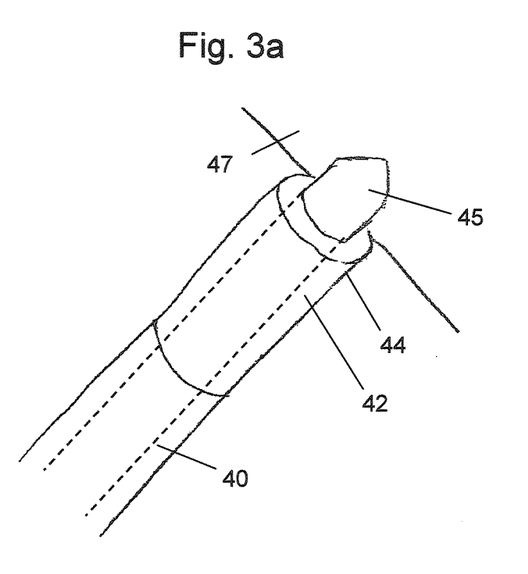
FIGS. 3a-b illustrate parts of a hydrogel anchoring system and steps of forming the hydrogel anchor within tissue.
Figure 3B:
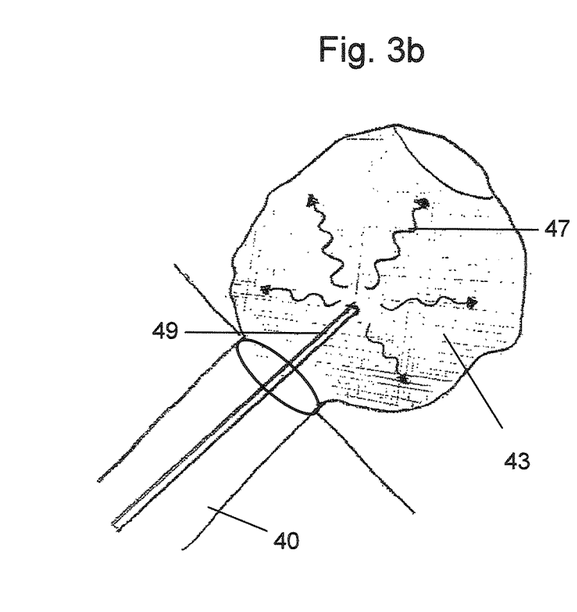

FIGS. 3a-b illustrates other embodiments of a silk hydrogel tissue anchor, and insertion of the hydrogel anchor into a target tissue. FIG. 3a shows a hollow tissue needle 40 having a puncturing member 45 at its distal end. Also at the distal end is a composition 42 including a polymerizable silk-containing hydrogel material and a photo-polymerization initiator, the composition encapsulated in a dissolvable sheath 44. The puncturing member 45 of the tissue needle 40 is shown penetrating a pelvic tissue 47.

Upon entry into the tissue the dissolvable sheath dissolves and releases the composition containing the polymerizable silk-containing hydrogel material in the tissue. The puncturing member 45 can be withdrawn from the tissue and moved back through the hollow tissue needle 40. An optic fiber 49 can then be moved through the hollow tissue needle 40 to place its distal end within the hydrogel material. Light can then be transmitted through the optic fiber to provide light irradiation 47 throughout the composition causing activation of the polymerization initiator and polymerization of the silk-containing hydrogel material.

Figure 4A:
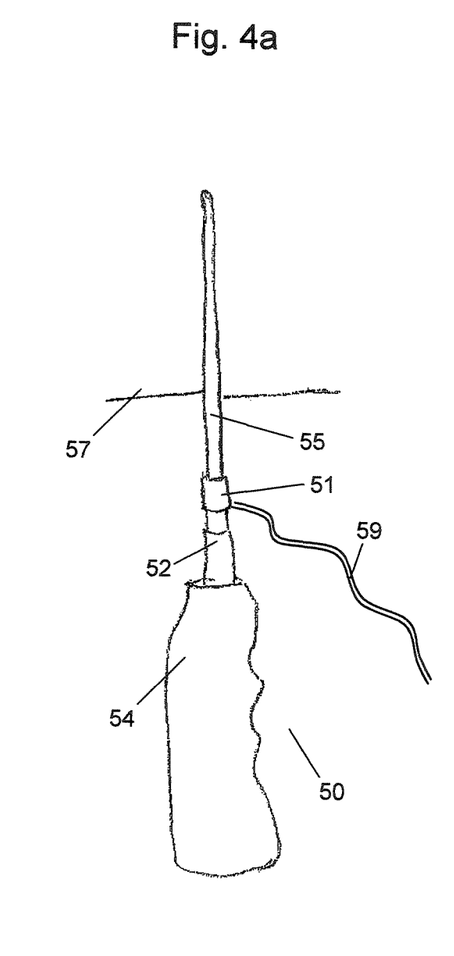
FIGS. 4a-c illustrate parts of a hydrogel anchoring system and steps of forming the hydrogel anchor within tissue.
Figure 4B:
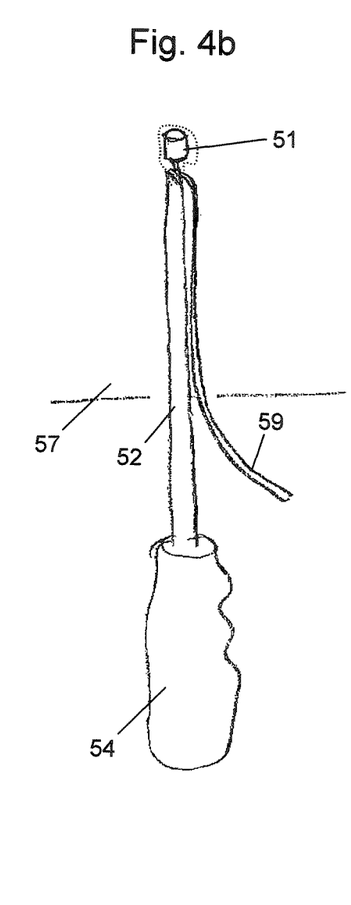
Figure 4C:
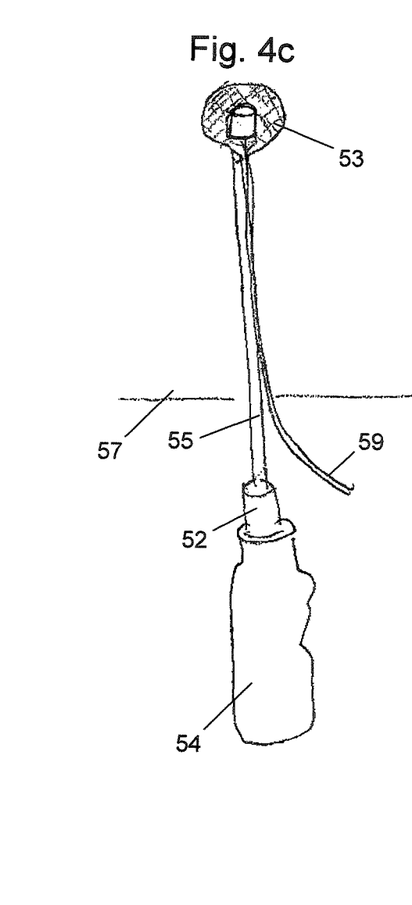

FIGS. 4a-c illustrates other embodiments of a tissue anchor system including a silk hydrogel composition. FIG. 4a shows a delivery tool 50 that includes a handle 54, and a needle 55 sufficient to puncture a tissue 57. Slidable along the shaft of the needle is a tissue anchor 51, which can have a cylindrical shape. The tissue anchor can be attached to a tether 59, which in some cases can be a thin strap of material. In some cases, the tether 59 may connect the tissue anchor 51 to a supportive mesh (not shown). The delivery tool 50 also includes a slidable sheath 52 that is slidable in proximal and distal directions.

FIG. 4b shows that the after the needle has entered a target tissue, the slidable sheath 50 can be moved in a proximal to distal direction, which, in turn, pushes the tissue anchor 51 towards the distal end of the needle 55. Activating a trigger on the handle will advance the sheath 50 in a distal direction. The tissue anchor 51 can be pushed off the distal end of the needle 55 and into the tissue. The tether 59, being attached to the tissue anchor 51, is pulled through the tissue as the tissue anchor 51 is advanced in a distal direction. The slidable sheath 52, extended fully distally, forms a conduit that is large enough to include the needle 55 and additional space around the needle to allow flow of a composition that includes the silk-containing hydrogel material. Hydrogel composition can be delivered into the tissue through the conduit formed by the slidable sheath 52. Alternatively, the needle 55 is hollow and can deliver the hydrogel composition to the tissue site at the distal end of the needle.

The reacting agent can then be passed down the needle to cross-link the anchor solution. This might consist of passing an optical fiber down the needle and then activating a UV source, or the fiber may already be integrated into the bore of the needle (with space for solution to pass around). A redox solution might also be injected down the needle to cause cross linking of the solution. Alternatively, the anchoring solution and REDOX solution can be mixed and injected simultaneously.

The hydrogel composition can be crosslinked in any one of a number of ways. For example, in some cases an optical fiber is moved down the needle and then the composition is activated by transmitting light to the distal end of the needle using a UV source, which can activate a polymerization photoinitiator in the composition. Alternatively, fiber can be integrated into the bore of the needle (with space for solution to pass around). Yet in another embodiment, the tether and UV fibers are passed to the anchoring site with additional needles or trocars.

In another mode of activation, a redox solution is delivered to the tissue site via needle to cause cross linking of the hydrogel material. Alternatively, the hydrogel composition and REDOX solution can be mixed and injected simultaneously.

FIG. 4c illustrates that an area in the tissue that includes a matrix 53 of crosslinked hydrogel material, with the tissue anchor 51 embedded within the matrix. FIG. 3c also illustrates the slidable sheath 52 withdrawn from the tissue. After the procedure has been completed, the needle 55 can be removed from the tissue.

In other embodiments, the needle 55 or slidable sheath 52 includes a port positioned between the distal and proximal ends of the needle or sheath, from which the hydrogel composition can emerge. In methods for anchoring, the tethering component is advanced to a portion of the needle or sheath containing a side port where the hydrogel composition can emerge.

In other modes of practice, if the tissue site for anchoring is close to the surface of the body and the hydrogel composition can be activated by UV light passed through the tissues.

In some embodiments the system can: 1) deliver a crosslinkable anchoring component 2) deliver a feature of the implant to be anchored; and 3) deliver the cross-linking agent (either UV light or REDOX solution).

In alternate embodiments, the tethering component is not advanced to the end of the needle but to a portion of the needle containing a side port where the anchoring solution can emerge.

In another embodiment, the anchor solution at an anchoring site close to the surface of the body can be activated by UV light passed through the tissues.

In another embodiment, the tether and UV fibers are passed to the anchoring site with additional needles or trocars.

Example 1

Mesh Adhesive

Use of the crosslinkable chemical system and combination with mesh was performed in vitro on chicken breast material, synthetic hydrogels, and in a cadaver. Several formulations of the crosslinkable chemical system were very successful in attaching to the tissue. Small pieces of mesh were able to adhere to the tissue with UV light curing and held over 4.0 pounds of force when pulled upon without tearing away or damaging the tissue.

The coating mixture contained the following components: trimethylolpropane ethoxylate (14/3 EO/OH) triacrylate; 2,2-dimethoxy-2-phenylacetophenone; 2-hydroxy-4'-(2-hydroxyethyl)-2-methylpropiophenone; isopropyl alcohol, and water Both a liquid/oil coating and a solid coating were applied to the mesh; both of these coatings strongly adhered to tissue.

The anterior and posterior vaginal planes of a small female cadaver were dissected. The mesh was then smoothed over the anterior side of the vagina and the light fiber pressed onto the mesh and into the vaginal tissue. The UV light was activated briefly (<1 sec). This was repeated around the anterior portion of the vagina to "tack" the mesh in place.

A few drops adhesive were added to "dry" portions of the mesh and then the light was then held 1" from the mesh and activated for ~10-15 sec while moving the light across the mesh surface to adhere the whole surface.

The steps were repeated for the posterior plane of the vagina.

The attachment strength was then tested using a force gage attached to the end of the mesh and pulling caudally. The some portions of the adhesive were seen to release at >4 lbs of tension on the mesh at which point the attachment test was halted.

The mesh was then attached to the sacral promontory and trimmed.

What is claimed is:

1. A pelvic implant comprising:
a support portion,
an extension portion extending from the support portion, and
a pelvic tissue treatment composition contactable with the extension portion of the implant, the composition comprising a water-soluble fibroin and a water-soluble crosslinkable or crosslinked polymer, and a dissolvable sheath encapsulating the pelvic tissue treatment composition,
wherein the support portion, extension portion, or both, comprise a mesh material, and the pelvic tissue treatment composition is crosslinkable to form a tissue anchor associated with the mesh material.

2. The implant of claim 1, wherein the pelvic tissue treatment composition comprises a light-activated polymerization initiator.

3. The implant of claim 2, wherein the light-activated polymerization initiator is selected from a group consisting of: benzophenones, anthraquinones, benzoins, acetophenones, and phosphate and antimonate salts.

4. The implant of claim 1, wherein the pelvic tissue treatment composition comprises an active agent that promotes tissue growth.

5. The implant of claim 4, wherein the active agent is a polypeptide, a polysaccharide, or a polynucleotide that promotes a tissue response.

6. The implant of claim 1, wherein the water-soluble crosslinkable or crosslinked polymer is selected from trimethylolpropane triacrylate, trimethylolpropane trimethacrylate, trimethylol propane tetraacrylate, monosaccharide acrylates, oligosaccharide acrylates, tetraethylene glycol diacrylate, and zinc acrylate.

7. The implant of claim 1, wherein the pelvic tissue treatment composition is a hydrogel.

8. The implant of claim 7, wherein the hydrogel is in the form of a filament, a string, a tube, a cotton puff, a helix, or a bubble.

9. The implant of claim 7, wherein the hydrogel is encapsulated by a polymer that dissolves in contact with body fluids.

10. A system for treatment of a pelvic condition, the system comprising:
a pelvic implant including a support portion and an extension portion;

a pelvic tissue treatment composition comprising a water-soluble fibroin, a water-soluble crosslinkable or crosslinked polymer, and a photo-polymerization initiator;
a delivery needle comprising a lumen configured to accommodate the composition and at least a portion of the extension portion of the pelvic implant;
a puncturing member at a distal end of the delivery needle; and
a dissolvable sheath encapsulating the pelvic tissue treatment composition.

11. The system of claim 10, wherein the pelvic tissue treatment composition is a hydrogel configured to promote tissue growth.

12. The system of claim 10, wherein the pelvic tissue treatment composition is disposed on the puncturing member.

13. The system of claim 12, wherein at least a portion of the pelvic tissue treatment composition is released from the puncturing member upon dissolution of the dissolvable sheath.

14. The system of claim 13, wherein the puncturing member is retractable through the lumen of the delivery needle.

15. The system of claim 14, further comprising an optic fiber movable into the pelvic tissue treatment composition through the lumen.

16. A system for treatment of a pelvic condition, the system comprising:
a pelvic implant comprising a tissue anchor attached to an extension portion of the implant;
a pelvic tissue treatment composition comprising a water-soluble fibroin and a water-soluble crosslinkable or crosslinked polymer; and
a delivery tool comprising a handle, a needle, and a slidable sheath that is slidable in a proximal direction and a distal direction along the needle,
wherein the needle is configured to puncture a tissue, the tissue anchor is slidable along the needle by movement of the slidable sheath, and the slidable sheath forms a conduit to allow flow of the pelvic tissue treatment composition.

17. The system of claim 16, wherein the pelvic tissue treatment composition is a hydrogel.

18. The system of claim 17, wherein the hydrogel is encapsulated by a polymer that dissolves when contacted with body fluids.

19. The system of claim 16, wherein the tissue anchor has a cylindrical shape.

20. The system of claim 16, wherein the tissue anchor includes a tether.

* * * * *